(12) United States Patent
Cupo et al.

(10) Patent No.: US 8,415,095 B2
(45) Date of Patent: Apr. 9, 2013

(54) USE OF NUCLEOSIDE DERIVATIVES COMPRISING A CITRATE GROUP FOR THE PRODUCTION OF ANTIBODIES HAVING AN AFFINITY FOR TRIPHOSPHORYLATED NUCLEOSIDES

(75) Inventors: Anny Cupo, Juan-les-Pins (FR); Cecile Le Saint, Vallauris (FR); Jean-Pierre Vincent, Cagnes-sur-Mer (FR); Fatima Akeb, Nice (FR); Daniele Duval, Nice (FR); Roger Guedj, Villefranche-sur-Mer (FR)

(73) Assignee: Centre National de la Recherche-Scientifique-CNRS (FR)

( * ) Notice: Subject to any disclaimer, the term of this patent is extended or adjusted under 35 U.S.C. 154(b) by 1107 days.

(21) Appl. No.: 10/933,628

(22) Filed: Sep. 3, 2004

(65) Prior Publication Data
US 2005/0130270 A1 Jun. 16, 2005

Related U.S. Application Data

(63) Continuation of application No. PCT/FR03/00708, filed on Mar. 5, 2003.

(51) Int. Cl.
*C12Q 1/68* (2006.01)
*G01N 33/53* (2006.01)
(52) U.S. Cl. ......... 435/6; 435/7.1; 435/91.2; 424/184.1; 514/42; 530/807; 536/22.1
(58) Field of Classification Search ............... 424/184.1; 435/6, 7.1, 91.2; 514/42; 530/807; 536/22.1
See application file for complete search history.

(56) References Cited

U.S. PATENT DOCUMENTS 5,380,825 A 1/1995 Stenglein et al.

OTHER PUBLICATIONS

Robbins et al., 1998. Development of a new cartridge radioimmunoassay for determination of intracellular levels of lamivudine triphosphate in the peripheral blood mononuclear cells of human immunodeficiency virus-infected patients. Antimicrobial Agents and Chemotherapy 42: 2656-2660.*
T. Brossette et al., "Synthesis of Analogues of 5'-Mono-, 5'-Di-, and 5'-Triphosphate-AZT for the Development of Specific Enzyme Immunoassay for Monitoring of Intracellular Levels of AZT-MP, AZT-DP, and AZT-TP," *Nucleosides & Nucleotides*, 1999, vol. 18, Nos. 4-5, pp. 939-940.
K. Cucumel et al., "Production and Characterization of Site-Directed Antibodies Against Dermorphin and Dermorphin-Related Peptides," *Peptides*, 1996, vol. 17, No. 6, pp. 973-982.
A. Cupo et al., "Detection of Methionine-Enkephalin at the 10-[16] Mole Level," *Journal of Neuroimmunology*, 1985, vol. 8, pp. 57-67.
A. Cupo et al., "Quantitation and Localization of MET-Enkephalin-ARG-GLY-LEU in Rat Brain Using Highly Sensitive Antibodies," *Neuropeptides*, 1984, vol. 4, pp. 389-401.
A. Cupo et al., "Monoclonal Antiidiotypic Antibodies against δ Opioid Receptors as an Electron Microscopy Probe," *European Journal of Cell Biology*, 1992, vol. 57, pp. 273-284.

(Continued)

*Primary Examiner* — Gail R Gabel
(74) *Attorney, Agent, or Firm* — DLA Piper LP (US)

(57) ABSTRACT

Nucleoside analogues comprising a citrate group can be used to obtain immunogens designed to produce antibodies having an affinity for triphosphorylated nucleosides. Such antibodies are useful for implementing sensitive immunologic assays for triphosphorylated nucleoside derivatives.

8 Claims, 9 Drawing Sheets

2',3'-didésoxyadénosine-5'-triphosphate (ddATP)

5'-O-(3,4-dicarboxy-3-hydroxy)butanoate-2',3'-didésoxyadénosine

OTHER PUBLICATIONS

A. Cupo et al., "Monoclonal Antiidiotypic Antibodies which Recognized the Binding Site of Delta Receptor: Fine Specificity of the Antiidiotypic Antibodies," *Progress in Opioid Research, National Institute on Drug Abuse*, 1986, pp. 25-23.

A. Cupo et al., "A New Immunological Approach to the Detection and the Quantification of the MET$^5$-Enkephalin Precursors in Rat Brain," *Neuropeptides*, 1984, vol. 4, pp. 375-387.

A. Cupo et al., "A New Immunization Procedure for the Obtention of Anti-Leucine Enkephalin Antibodies: Part I. Immunization Procedure and Physicochemical Characteristics of Antibodies," *Neuropeptides*, 1986, vol. 8, pp. 207-219.

B. Ferrua et al., "Measurement of the Anti-HIV Agent 2',3'-Didehydro-2',3'-Dideoxythymidine (D4T) by Competitive ELISA," *Journal of Immunological Methods*, 1994, vol. 176, pp. 103-110.

I. Garreau et al., "Hemorphin Peptides Are Released form Hemoglobin by Cathespin D. Radioimmunoassay Against the C-Part of V-V-Hemorphin-7: An Alternative Assay for the Cathepsin D Activity," *Peptides*, 1997, vol. 18, No. 2 pp. 293-300.

L. Goujon et al., "Monitoring of Intracellular Levels of 5'-Monophosphate-AZT Using an Enzyme Immunoassay", *Journal of Immunological Methods*, 1998, vol. 218, pp. 19-30.

S. Kaul et al., "Specific Radioimmunoassays for the Measurement of Stavudine in Human Plasma and Urine," *Journal of Pharmaceutical and Biomedical Analysis*, 1996, vol. 15, pp. 165-174.

G. Köhler et al., "Continuous Cultures of Fused Cells Secreting Antibody of Predefined Specificity," *Nature*, Aug. 7, 1975, vol. 256, pp. 495-497.

C. Périgaud et al., "Nucleoside Analogues as Chemotherapeutic Agents: A Review," *Nucleosides and Nucleotides*, 1992, vol. 11, Nos. 2-4, pp. 903-945.

B. L. Robbins et al., "Quantification of Intracellular Zidovudine Phosphates by Use of Combined Cartridge-Radioimmunoassay Methodology," *Antimicrobial Agents and Chemotherapy*, Nov. 1996, vol. 40, No. 11, pp. 2651-2654.

M. Saady et al., "First Synthesis of Fully Deprotected Diimitriphosphoric Acid and Derivatives Designed for the Synthesis of "PNPNP" Nucleotides and Dinucleotides", *J. Org. Chem.*, 1995, vol. 60, pp. 3685-3691.

R. Weaver et al., "The Design and Synthesis of Nucleoside Triphosphate Isosteres as Potential Inhibitors of Reverse Transcriptase," *Tetrahedron*, 1997, vol. 53, No. 15, pp. 5537-5562.

R. Weaver. et al., "Isosteres of nucleoside triphosphates", *Bioorganic & Medicinal Chemistry Letters, Oxford*, vol. 6, No. 20 Oct. 22, 1996 pp. 2405-2410.

T. Brossett et al., "Synthesis of polyphosphorylated AZT derivatives for the development of specific enzyme immunoassay", *Journal of Organic Chemistry, American Chemical Society*, Easton, vol. 64, 1999, pp. 5083-5090.

Fatima Akeb et al., "The production and evaluation of antibodies for enzyme immunoassay of AZTTP", Nucleosides Nucleotides & Nucleic Acids, pp. 243-250,vol. 20, No. 3, Mar. 2001 pp. 243-250.

* cited by examiner

2',3'-didésoxyadénosine-5'-triphosphate (ddATP)

5'-O-(3,4-dicarboxy-3-hydroxy)butanoate-2',3'-didésoxyadénosine

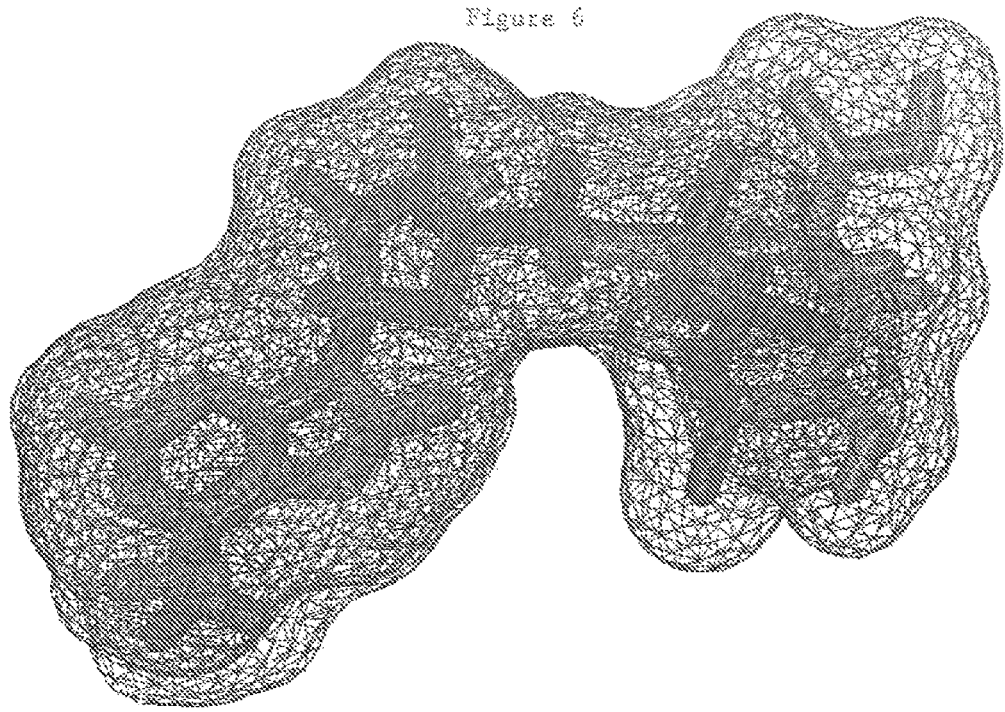
Figure 6
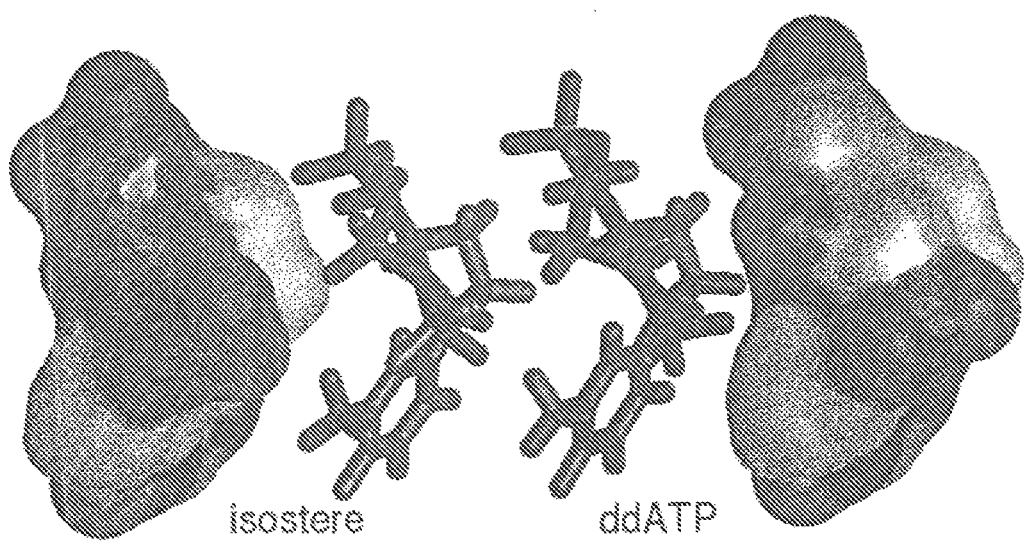
isostere ddATP

Allyl = CH$_2$CH=CH$_2$

☐ Rabbit 5 (Titre : 1/5900)
■ Rabbit 6 (Titre : 1/258000)

△ ddA-HS (IC 50 = 1,1.10$^{-10}$M)
▨ ddA (IC 50 = 4,3.10$^{-10}$M)
▲ ddA-HS-KY (IC 50 = 6.10$^{-10}$M)
● isostère of ddATP (IC 50 = 5,2.10$^{-11}$M)
☐ ddATP (IC 50 = 1,1.10$^{-9}$M)
○ ATP (IC 50 = 3,6.10$^{-5}$M)

USE OF NUCLEOSIDE DERIVATIVES COMPRISING A CITRATE GROUP FOR THE PRODUCTION OF ANTIBODIES HAVING AN AFFINITY FOR TRIPHOSPHORYLATED NUCLEOSIDES

CROSS REFERENCE TO RELATED APPLICATIONS

This application is a continuation of International Application No. PCT/FR03/00708, with an international filing date of Mar. 3, 2003 (WO 03/07509, published Sep. 12, 2003), which is based on French Patent Application No. 02/02782, filed Mar. 5, 2002.

FIELD

This disclosure pertains to the use of nucleoside analogues comprising a citrate group for the production of antibodies having an affinity for triphosphorylated nucleosides.

BACKGROUND

Certain nucleosides are currently employed as antiviral agents, or as anticancer agents and it is known that they must be metabolized in their triphosphorylated form in order to exert an antiviral or anticancer inhibitory activity.

In the context of antiviral treatments, notably in anti-HIV therapies, it is important to quantify these triphosphorylated forms of the nucleoside analogues.

Thus, with the goal of quantifying the active form of the nucleoside analogues, it is essential to use sensitive quantitative determination methods that are specific to said triphosphorylated nucleosides, referred to below as "ddNTPs."

One of the determinant factors of the therapeutic failure of anti-HIV treatments can be explained by an alteration of the cellular metabolism for nucleosides (ddNs), which leads to an insufficient concentration of the active molecule in the intracellular medium. Therefore, one of the means of controlling loss of therapeutic efficacy would be the determination of the intracellular concentration of these molecules (triphosphorylated nucleosides and antiproteases) by immunological determinations. The therapeutic drug monitoring (TDM) of patients can then be envisaged for optimizing the administration of these molecules by proposing personalized treatments, but also being able to evaluate drug combinations.

The very intense catabolism of the antiproteases by the hepatic and intestinal enzymes, as well as the mechanisms of excretion, result in the administration of extremely high doses of antiviral agents to patients which can lead to devastating side effects.

The problem is different with regard to the nucleoside analogues. The doses administered are very high because of the limited penetration of the precursor into cells. The different phosphorylated metabolites of the drug will thus affect not only the viral polymerases, but also the cellular polymerases. The toxicity of the catabolites of the drug will be added to the nonspecificity of the nucleoside analogues. In anti-HIV treatment, because of the high quantities of antiviral agents administered to the patients, drug catabolites would affect a large number of cellular compartments including those which are reserved for the differentiation of the stem cells, thereby inducing the side effects which make anti-HIV treatments so constraining and uncomfortable.

Thus, the plasma and intracellular levels of those anti-HIV molecules which are used most often in combination directly reflect the metabolism of the entire organism. Thorough knowledge of the plasma and intracellular levels of these anti-HIV molecules is essential, and differs from individual to individual and even over time in the same patient.

Measurement of these parameters would enable clinicians to determine the consequences of combination regimes, and to optimize the use of anti-HIV drugs and to adjust the dosage as a function of the patient and the evolution of his disease. It is therefore important for the clinician to have access to the measurement of the intracellular content, which has a very close relationship with the plasma concentration and viral load. This viral load has a direct impact on the therapeutic success.

Methods of intracellular quantitative determinations of nucleoside derivatives have been developed; See, e.g., Robbins, B. L. et al. (1996) "Quantification of intracellular zidovudine phosphates by use of combined cartridge-radioimmunoassay methodology". Antimicrob. Agents Chemother. 40, 2651-2654; Goujon, L. et al. (1998) "Monitoring of intracellular levels of 5'-monophosphate-AZT using an enzyme immunoassay". J. Immunol. Methods, 218, 19-30; Robbins, B. L. et al. (1998) A. "Development of a new cartridge radioimmunoassay for determination of intracellular levels of lamivudine triphosphate in the peripheral blood mononuclear cells of human immunodeficiency virus infected patients". Antimicrob. Agents Chemother. 42, 2656-2660).

However, these methods do not have adequate test sensitivity, which is especially required for detecting the low concentrations of nucleoside analogues present in the cell compartments and available in small samples.

Although methods exist for the measurement of nucleosides using HPLC and CE (capillary electrophoresis), the exciting methods are difficult to apply for the therapeutic monitoring of patients. These existing methods require a meticulous preparation of the samples, involve a lengthy analysis time and need a large blood volume to enable detection of the low intracellular levels. Furthermore, the investment costs required for purchasing the equipment and reagents for its operation, such as solvents and columns, represents a major drawback for laboratories and hospitals.

With regard to the phosphorylated derivatives of nucleoside analogues, there does not exist a method of chromatographic determination. In contrast, immunologic methods exist but they are indirect and require multiple steps, among others the purification of the phosphorylated metabolites, enzymatic dephosphorylation or elimination of the salts and reagents. (Robbins, B. L. et al. (1996) "Quantification of intracellular zidovudine phosphates by use of combined cartridge-radioimmunoassay methodology". Antimicrob. Agents Chemother. 40, 2651-2654; Goujon, L. et al. (1998) "Monitoring of intracellular levels of 5'-monophosphate-AZT using an enzyme immunoassay". J. Immunol. Methods, 218, 19-30; Robbins, B. L. et al. (1998) A. "Development of a new cartridge radioimmunoassay for determination of intracellular levels of lamivudine triphosphate in the peripheral blood mononuclear cells of human immunodeficiency virus infected patients". Antimicrob. Agents Chemother. 42, 2656-2660).

Moreover, certain methods have been envisaged for obtaining such antibodies, e.g., antibodies directed against AZT-TP, using as immunogen an AZT-TP derivative whose phosphoric anhydride bonds have been substituted by methylene phosphonate bonds (or P—$CH_2$—P). The methylene-bis-phosphonate group (P—$CH_2$—P—$CH_2$—P) possesses structural characteristics close to those of the pyrophosphate group (P—O—P—O—P), since the angle of the phosphoric anhydride bond (P—O—P) is 130°, that of the methylene phosphonate bond is 117°; the length of the P—O bonds is 1.61 Å and that of the P—C bonds is 1.79 Å. (Saady et al. (1995), "First synthesis of fully deprotected diimidotriphosphoric acid and derivatives designed for the synthesis of "PNPNP" nucleotides and dinucleotides". J. Org. Chem. Vol. 60, pp 3685-3691).

However, the affinity of the different antibodies directed against this methylene-bis-phosphonate analogue of AZT-TP is not sufficient to enable its quantification, especially since the intracellular quantities of nucleotides are extremely small and the sample volume is also reduced.

SUMMARY

We provide an immunogen including a citrate derivative of a nucleoside coupled to a carrier molecule.

We also provide a method for producing an antibody having an affinity for a ddNTP derivative, including the following steps: a) immunizing an animal with at least one immunogen and b) purifying the resultant polyclonal antibodies.

We further provide to a method for producing an antibody having an affinity for a ddNTP derivative, including the following steps: a) immunizing immunocompetent cells from an animal with at least one immunogen, b) immortalizing cells secreting antibodies having an affinity for the ddNTP derivative by means of a cellular fusion of cells from the animal isolated from the spleen or lymphatic ganglia with a fusion cell line, c) identifying and selecting immortalized hybridomas secreting the antibodies having an affinity for the ddNTP derivative, and d) purifying of the antibodies produced by the hybridomas.

We still further provide an antibody having an affinity for the immunogen.

We still yet further provide a method for the quantitative determination of a ddNTP derivative, including the steps of: a) bringing into contact at least one antibody with a sample including the ddNTP derivative, optionally in the presence of a tagged tracer, b) separating the complex constituted by the antibody bound to the ddNTP derivative from the unbound ddNTP derivative, and c) Measuring the ratio between the quantity of the ddNTP derivative bound by the antibody versus the unbound ddNTP derivative.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 6 illustrates the molecular modeling which confirms that the resultant molecule from the coupling of 2-hydroxy-2,3-allyloxycarbonylbutanoic acid on the 5' position of the ddA possesses structural and electronic characteristics close to those of ddATP. The top shows the superposition of the structures of ddATP and the isostere of ddATP.

FIG. 9 generally illustrates the characteristics of the anti-isostere antibody of ddATP in RIA test with the tracer dd-A-HS-(Y*-K). Specifically.

DETAILED DESCRIPTION

Figure 1:
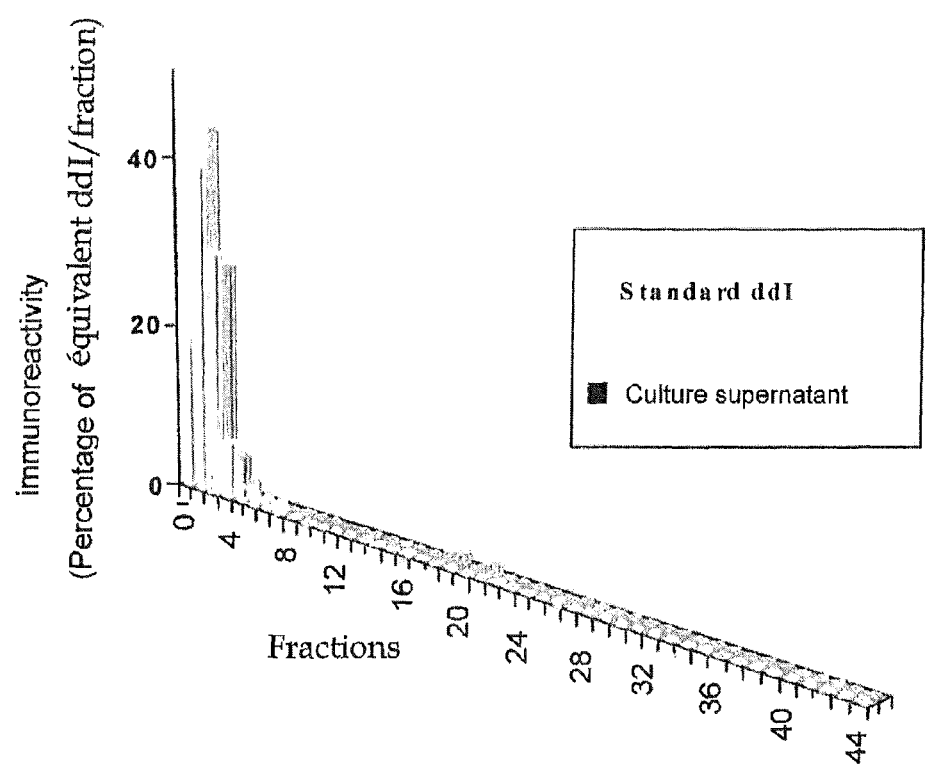
FIG. 1 is a graph showing the determination of the nature of the immunoreactive material present in the culture supernatant by chromatography on anionic cartridge and radioimmunological detection. At left: Immunoreactivity (percentage of ddI equivalent/fraction); In box: ddI standard/culture supernatant.

The following meanings are understood for the following terms:

natural nucleoside: a molecule constituted by the association of a purine base (adenine or guanine) or pyrimidine base (cytosine, uracil and thymine) with a pentose residue (beta-D-ribofuranose or beta-D-deoxyribofuranose);

nucleoside analogue (ddNs): any molecule composed of an optionally modified base coupled to a ribose or a ribose analogue.

Such analogues are, e.g., those described in the document: Périgaud, C. et al. Nucleosides and Nucleotides 1992, vol. 11(2-4), pages 903-945, the entire disclosure of which is herein incorporated by reference.

Thus, in relation to a natural nucleoside, an analogue can comprise modifications of the ribose, such as e.g., those mentioned on page 907 of the previously cited document, such as the substitution of one or more atoms, the displacement of the bond between the base and the sugar, anomeric inversions (beta-alpha), addition of various functions, inversion, substitution or elimination of hydroxyl groups, modification of the size of the ring (pyranose), inversion of the configuration (D-L) or rupture of the ring (acyclonucleosides) or modifications of the heterocyclic base such as, e.g., indicated on page 908 of said document, for the analogues: Fura, FdUrd, Thi-Gua, 6-MP, AraC or fludarabine phosphate.

As used herein, the term "nucleoside" employed in the text designates without distinction either a natural nucleoside or a nucleoside analogue such as defined above.

We provide methods for the quantification of nucleoside analogues that can overcome the drawbacks of the existing assays for such compounds which are used, for example, as antiviral compounds.

The methods for the quantification of nucleosides by means of immunological determinations employed present numerous advantages in terms of sensitivity and rapidity, because both the time required for preparation of the sample and the time required for the determination itself are considerably reduced with respect to previous methods.

The methods are moreover applicable to a large number of small samples both in terms of volume and number of cells. The methods include a quantification method that can be performed in a complex mixture and which is sensitive, suitable for weak intracellular concentrations, rapid and suitable for monitoring patients in the hospital environment.

Few studies have focused on the intracellular metabolism of nucleosides because of the instability of the triphosphorylated derivatives, due to the fact that the pyrophosphate bonds are sensitive to hydrolysis and rapidly degraded.

We thus provide a method for the preparation of antibodies for the determination of ddNTP derivatives, which antibodies recognizing the ddNTP derivatives with sufficient affinity to enable intracellular quantification of the ddNTP derivatives.

Furthermore, these antibodies do not recognize the endogenous nucleotides.

Immunogens capable of inducing an immune response in mammals are thus provided. Such immunogens are prepared from nucleoside analogues presenting not only a structural analogy, but also an electronic analogy, with the molecule to be determined for immunization of mammals. The nucleoside analogues are referred to below as "isosteres."

Such isosteres of nucleoside triphosphates have already been described; e.g., for the conception of an inhibitor of the reverse transcriptase. (Weaver, R. and Gilbert, I. H. (1997) "The design and synthesis of nucleoside triphosphate isostere as potential inhibitors of HIV reverse transcriptase". Tetrahedron, vol. 53, 5537-5562; Weaver, R. et al. (1996) "Isosteres of nucleoside triphosphates". Bioorg. Med. Chem. Lett. Vol. 6, 2405-2410, the entire disclosures of which are herein incorporated by reference.)

We thus also provide the use of the isosteres of nucleoside triphosphates, preferably isosteres in which their phosphate group has been replaced by the citrate group, for the preparation of immunogens by coupling of the isosteres onto carrier molecules.

The advantage of this approach is that one obtains a better detection of the triphosphorylated molecule, because the antibody was produced against an isostere molecule presenting close structural and electronic analogies with said triphosphorylated derivative.

The immunization of immunocompetent cells of vertebrates, notably of mammals, enables production of antibodies having an affinity adapted to the levels of the ddNTP derivatives, including those which are only present at very low levels.

We thus provide an immunogen comprising a citrate derivative, of a nucleoside or a nucleoside analogue coupled to a carrier molecule.

The nucleoside or nucleoside analogue is preferably selected from among the group comprising: Acyclovir, adenosine, S-adenosyl-L-methionine, 2',3'-dideoxyadenosine (ddA), 2',3'-didehydro-2',3'-dideoxythymidine (d4T), 2',3'-dideoxyo-3'-thiacytidine (3TC), 3'-azido-3'-deoxythymidine (AZT), carbovir, cordycepin, cytidine, cytosine-b-D-arabinoside, deoxycytidine, deoxytubercidine, 2'-deoxyuridine, formycin A, formycin B, ganciclovir, guanosine, inosine, puromycin, ribavirin, sangivamycin, thymidine, tubercidin, uridine, abacavir, 3-fluoro-2',3'-dideoxythymidine (FLT), Fura, FdUrd, Thi-Gua, 6-MP, AraC or fludarabine phosphate.

Antimetabolic anticancer products are also suitable nucleosides or nucleoside analogues for use in the present methods, such as:
   analogues of purine bases, including 6-mercaptopurine, cladribine, fludarabine; and
   analogues of pyrimidine bases, including 5-fluorouracil, cytarabine, gemcitabine, tenofovir.

For the carrier molecule, it is possible to use any high molecular weight molecule, preferably between about 50,000 and about 500,000 daltons, which is capable of inducing an immune response. The carrier molecule can be selected from among a protein, such as a polypeptide phylogenetically remote from the animal species used for the immunization; or a polysaccharide.

The carrier molecule is preferably a protein selected from among the group consisting of ovalbumin, bovine albumin serum, limpet hemocyanin, thyroglobin, immunoglobulins, casein, hemoglobin, bacterial toxins (such as the subunit B of cholera toxin), tetanus toxin, diphtheria toxin and lectins (such as the subunit B of ricin).

We also provide the use of immunogens as defined above to produce specific antibodies of the citrate-nucleosides or citrate-nucleoside derivatives used for the immunization.

We also provide the use of immunogens as defined above to produce antibodies having an affinity for said ddNTP derivative.

We also provide a method for producing an antibody having an affinity for said ddNTP derivative.

This antibody can be a polyclonal antibody, in which case a method for its production can comprise the following steps:
   a) immunizing an animal with at least one immunogen of the invention; and
   b) purifying the polyclonal antibodies produced.

The animal immunized in step (a) is preferably a nonhuman mammal, for example a rodent, especially a rat or mouse; a goat; a rabbit; or a chicken, and the purification of the antibodies of step (b) can be performed from the blood of the immunized animal, or from the egg yolk in the case of a chicken.

The antibody can be a monoclonal antibody, in which case a method for its production can then comprise the following steps:
   a) immunizing immunocompetent cells from an animal with at least one immunogen of the invention;
   b) immortalizing cells secreting antibodies having an affinity for said ddNTP derivative by means of a cellular fusion of the cells from the animal in step a) with a fusion cell line;
   c) identifying and selecting the immortalized hybrid clones, also called hybridomas, secreting said antibodies having an affinity for said ddNTP derivative; and
   d) purifying the antibodies produced by said hybridomas.

According to particular aspects of the method for producing monoclonal antibodies, the immunocompetent cells of an animal; e.g., cells from the spleen or lymphatic ganglia of said animal, are immunized either in vivo or in vitro.

The fusion cell line used in step b) of the method for producing monoclonal antibodies is preferably selected from a mouse myeloma line, a rat myeloma line or cell lines enabling preparation of heterohybrids.

We also provide hybridomas produced in the manner described above, which are capable of synthesizing and secreting monoclonal antibodies having an affinity for a ddNTP derivative.

We also provide a specific antibody of the citrate-nucleoside isosteres, and in particular an anti-citrate-nucleoside antibody recognizing at least one immunogen of the invention.

We also provide an antibody having an affinity for a ddNTP derivative produced by any one of the above-described methods for producing antibodies.

The affinity of the antibodies for the ddNTP derivative against which it was prepared have an IC50 which is preferably greater than about $10^{-7}$, more preferable greater than about $10^{-9}$, and most preferably greater than about $10^{-10}$.

The term "IC50" is defined as the concentration of untagged antigen capable of inhibiting 50% of the antigen-antibody binding. The IC50 is a good reflection of the affinity, which can be determined by Scatchard's method.

We also provide an antibody fragment having an affinity for a ddNTP derivative comprising at least one variable part of a molecule of an antibody having the same affinity for said ddNTP derivative as said non-fragmented antibody molecule.

Such fragments are, e.g., the fragments Fv, Fab, Fab', $F(ab)_2$, $F(ab')_2$, which can be produced by enzymatic digestion or by chemical cleavage from non-fragmented antibodies by techniques known to the expert in the field. As used herein, "antibody" is understood to include antibody fragments.

We also provide recombinant immunoglobulins, their heavy and/or light chains or fragments thereof, which can be produced by recombining isolated nucleic acids coding for the heavy and/or light chains or functional fragments thereof and expressing said recombined nucleic acids in a prokaryote cellular host such as *E. coli* or in a eukaryote host such as yeast or in a mammalian cell. As used herein, "antibodies" is understood to include such recombinant immunoglobulins.

We also provide a method for the immunological quantification of triphosphorylated nucleoside derivatives.

These triphosphorylated derivatives are formed notably during the metabolism of nucleosides used in antiviral therapies, and in particular in anti-HIV therapies, but are also formed during anticancer treatments.

Such triphosphorylated derivatives include, e.g., triphosphorylated derivatives of AZT, F3dThd, IdUrd, AraA, virazole, acyclovir, DHPG or ganciclovir, d4T, 3TC, ddA and the diphosphorylated derivative of Tenofovir.

This method for the immunologic quantitative determination of the triphosphorylated nucleoside derivative by means of antibodies having an affinity for the derivative enables the quantification of a large number of samples. Because of the sensitivity of the method, only a small sample volume is required. In fact, the Applicant has been able to quantify in vitro the triphosphorylated derivative ddATP in $10^6$ to $4\times10^6$ CMSP previously incubated with variable concentrations of ddI ($10^{-7}$ to $10^{-9}$ M).

According to One preferred aspect of the method, the method for quantification of triphosphorylated nucleosides makes it possible to eliminate the supplementary steps required in the other methods, such as enzymatic degradation or purification on Sep-Pak C18 cartridge.

According to one preferred aspect, the method for the determination of a ddNTP derivative according to the invention comprises the following steps:
a) bringing into contact at least one antibody having an affinity for a ddNTP derivative of the invention with a sample comprising, or suspected of comprising said nucleoside triphosphate or an analogue thereof, optionally in the presence of a tagged tracer;
b) separating the complex formed by the antibody having an affinity for said ddNTP derivative bound to said ddNTP derivative from said free ddNTP derivative; and
c) measuring the ratio between the quantity of ddNTP bound by the antibody versus the unbound ddNTP derivative.

The tracer is preferably selected from among a derivative of the nucleoside to be detected, wherein the tracer comprises a motif that can be tagged. Suitable motifs that can be tagged include a motif comprising a tyrosine, a histidine or any amino acid or group possessing an amide function, which is preferably capable of introducing a radioactive element or is capable of being one, such as for example the Bolton-Hunter reagent.

A particularly preferred tracer comprises a dipeptide Tyr-Lys motif or a Lys-Tyr motif.

The tracer can be tagged by means of an enzyme, a chromophore, a colorant, a fluorophore, a particle, such as a metallic or magnetic particle, a pigment or a radioactive atom.

We further provide a method for the quantitative determination of a ddNTP derivative in a biological sample.

According to one aspect, the method for quantitative determination of the ddNTP derivative is performed on a biological fluid.

The biological fluid can include blood, plasma, serum, cerebrospinal fluid (CSF), urine, lymph or saliva.

According to another aspect, the method for quantitative determination of the ddNTP derivative is performed on a biological sample comprising cells.

The cells can be lymphocytes, peripheral monocytes, Langerhans' cells, dendritic cells, presenter cells, stem cells, adipocytes, immune cells, possibly sorted such as $CD4^+$ or $CD8^+$, or any other cell found in a biological sample.

According to a further aspect, the method for quantitative determination of the ddNTP derivative is a histological type quantification performed on a tissue section, such as ganglion tissue or on a cell element. The visualization of the directly- or indirectly-tagged antibody then allows observation of the localization and distribution of the ddNTP derivative in the target tissue.

The detection of the antiviral agents is then performed after fixation of the cells by different reagents intended to immobilize the molecules to be displayed at the cellular site where they are localized. These fixatives can be of any suitable type, such as succinic anhydride vapors, paraformaldehyde, glutaraldehyde or carbodiimides.

The method for the quantification of a ddNTP derivative is applicable to the determination of said derivatives in a patient who has been the object of an antiviral therapy with nucleoside analogues, notably in the framework of anti-HIV therapies. This method can also be used for the quantification of a ddNTP derivative formed in an individual who has been subjected to anticancer treatments which also use nucleoside derivatives as active agents.

Our methods are illustrated by means of the non-limiting examples discussed below, that describe using a nucleoside analog, ddATP. It is understood, however, that other nucleosides or nucleoside analogues can be used in the methods.

It is of course possible to adapt the method for the production of antibodies capable of detecting any triphosphorylated nucleoside analogue.

These non-limiting examples pertaining to the derivative ddATP are presented in detail below and with reference to the attached figures.

Examples

We provide a method for the quantification of 2',3'-didesoxyadenosine-5'-triphosphate or ddATP, the active metabolite of the ddI used as antiviral agent, by producing antibodies directed against an isostere molecule (derivative of ddATP) which possessed structural and electronic analogies to this molecule.

Figure 5:
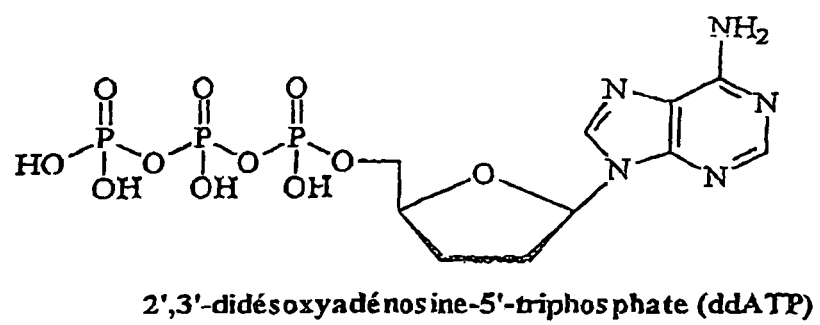
FIG. 5 shows the ddATP analogue and an isostere thereof in which the triphosphate group is substituted by the citrate group so as to lead to 5'-O-(3,4-dicarboxy-3-hydroxy)butanoate-2',3'-didesoxyadenosine.
Figure 5:
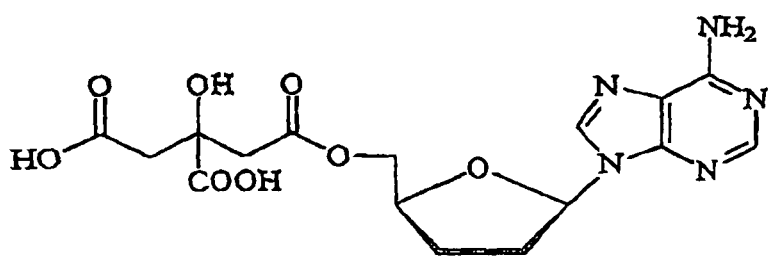

I. Preparation of the Derivative 5-O-(3,4-dicarboxy-3-hydroxy)butanoate-2',3'-didesoxyadenosine In this analogue of ddATP, the triphosphate group was substituted by the citrate group so as to lead to 5'-O-(3,4-dicarboxy-3-hydroxy)butanoate-2',3'-didesoxyadenosine (FIG. 5).

The molecular modeling confirmed that the molecule resulting from the coupling of the 2-hydroxy-2,3-allyloxycarbonylbutanoic acid on the 5' position of the ddA possessed structural and electronic characteristics close to those of ddATP (FIG. 6).

The synthesis of 5'-O-(3,4-dicarboxy-3-hydroxy)butanoate-2',3'-didesoxyadenosine required first the protection of two of the carboxylic acid function groups of the citric acid in allyl ester form.

The synthesis of 2-hydroxy-2,3-allyloxycarbonylbutanoic acid was performed according to the method described by Weaver, R. and Gilbert, I. H. (Tetrahedron, (1997), 53, 5537-5562. "The design and synthesis of nucleoside triphosphate isosteres as potential inhibitors of HIV reverse transcriptase," the entire disclosure of which is herein incorporated by reference.)

Figure 7:
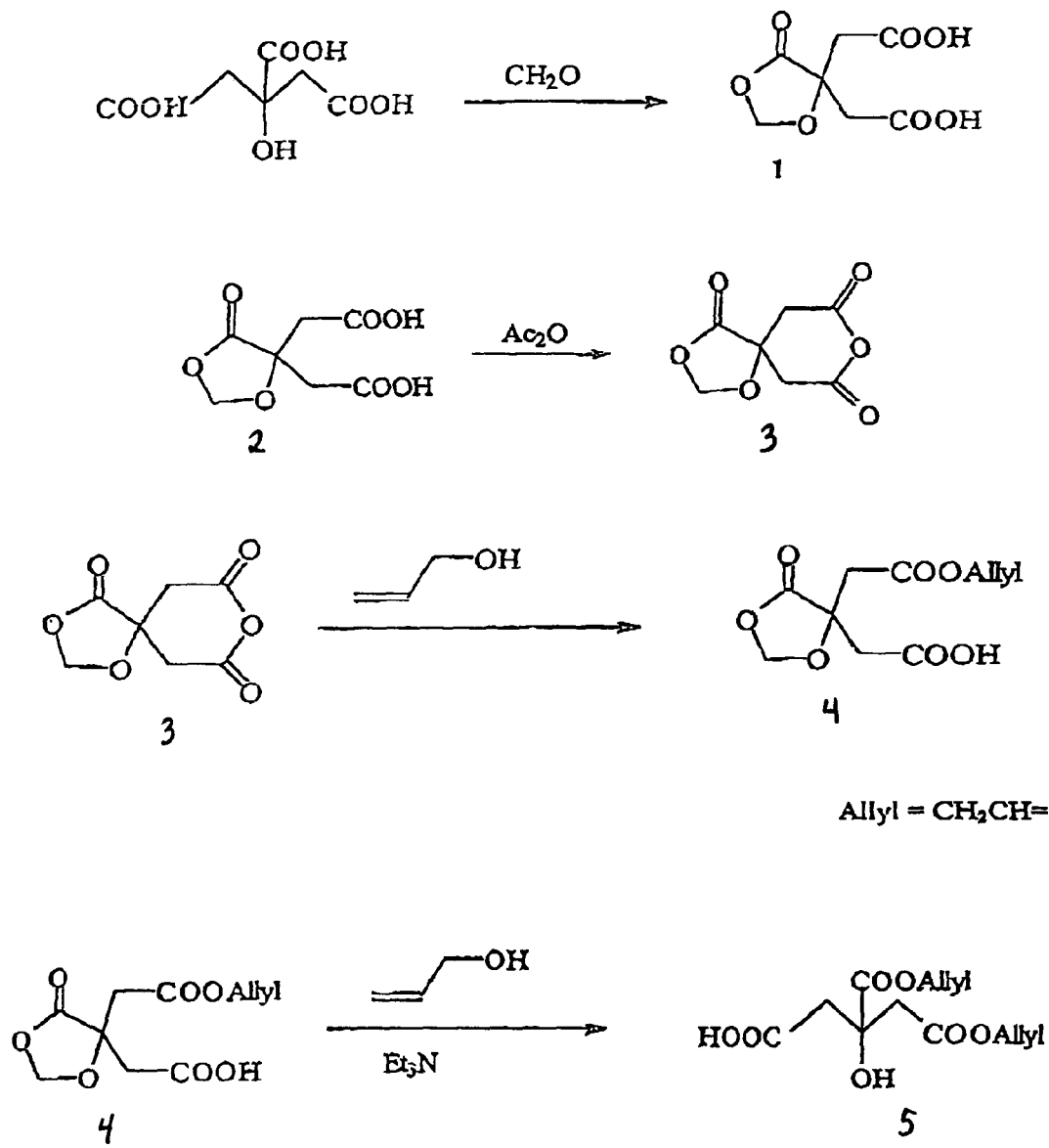
FIG. 7 is a diagram showing the synthetic pathway for producing the allyl diester of citric acid in four steps.

The preparation of 2-hydroxy-2,3-allyloxycarbonylbutanoic acid was performed in 4 steps:
a) formation of the oxalactone 1 by treatment of citric acid with paraformaldehyde,
b) cyclization of the diacid 2 into anhydride 3 by exchange with acetic anhydride,
c) production of the allyl monoester 4 by opening of the anhydride 3 by allyl alcohol; and
d) production of the allyl diester of citric acid 5 by opening of the lactone and hydrolysis of the methylene dioxy (FIG. 7).

The coupling conditions of the ddA to the 2-hydroxy-2,3-allyloxycarbonylbutanoic acid described in the previously cited article by Weaver R. et al. (1997) were not satisfactory because the coupling yield was very low, and was accompanied by the partial degradation of the product because of the dehydration of the β-hydroxy ester in basic medium.

Figure 8:
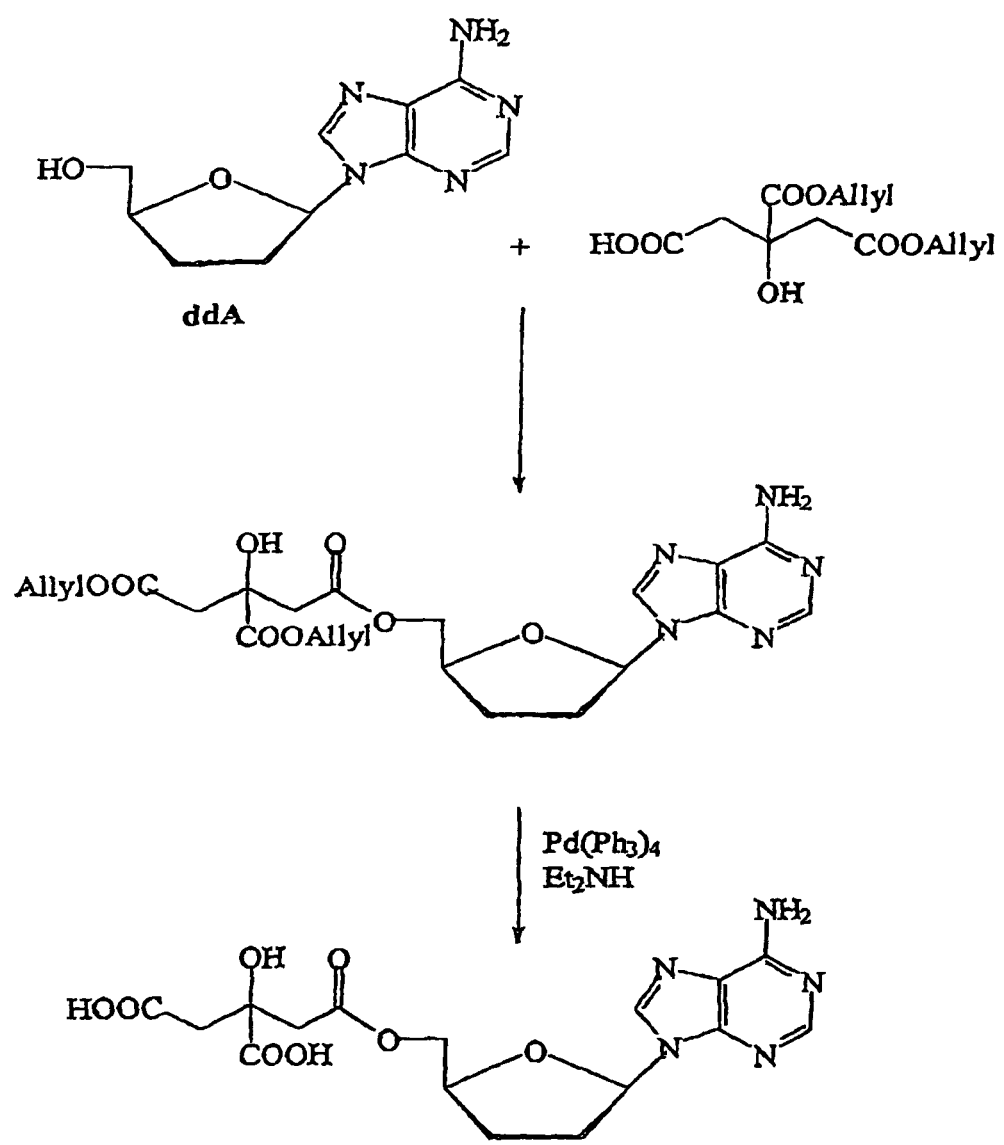
FIG. 8 shows the coupling of the ddA to 2-hydroxy-2,3-allyloxycarbonylbutanoic acid in the presence of dicyclohexylcarbodiimide (DCC) and 1-hyroxy-7-azabenzotriazole (HOAt) in tetrahydrofuran for the preparation of 5'-O-((3,4-diallyloxycarboxyl)-3-hydroxy)butanoate-2',3'-didesoxyadenosine.
Figure 9A:
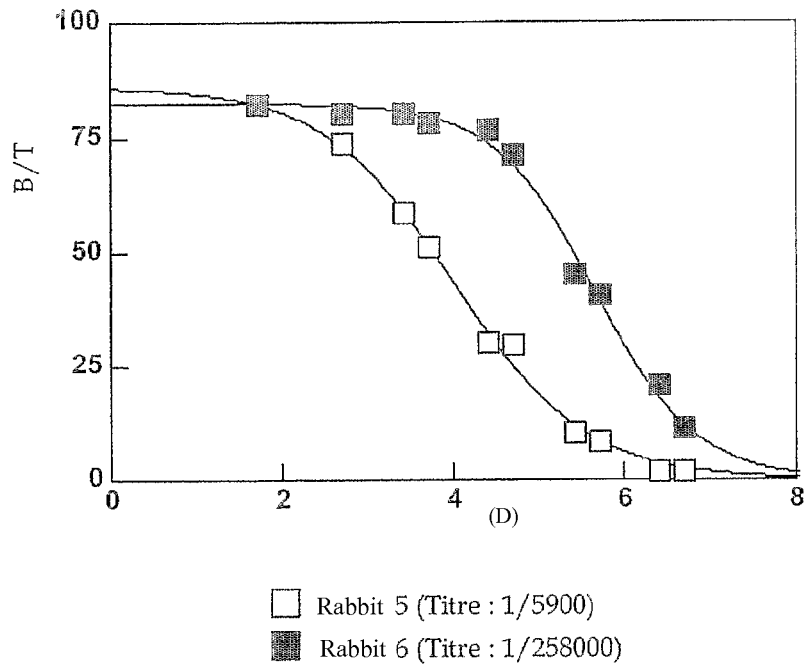
FIG. 9a is a graph showing the determination of the antibody titer. B/T: ratio of bound antigen versus free antigen; (D): log of the final antibody dilution. Specifically.
Figure 9B:
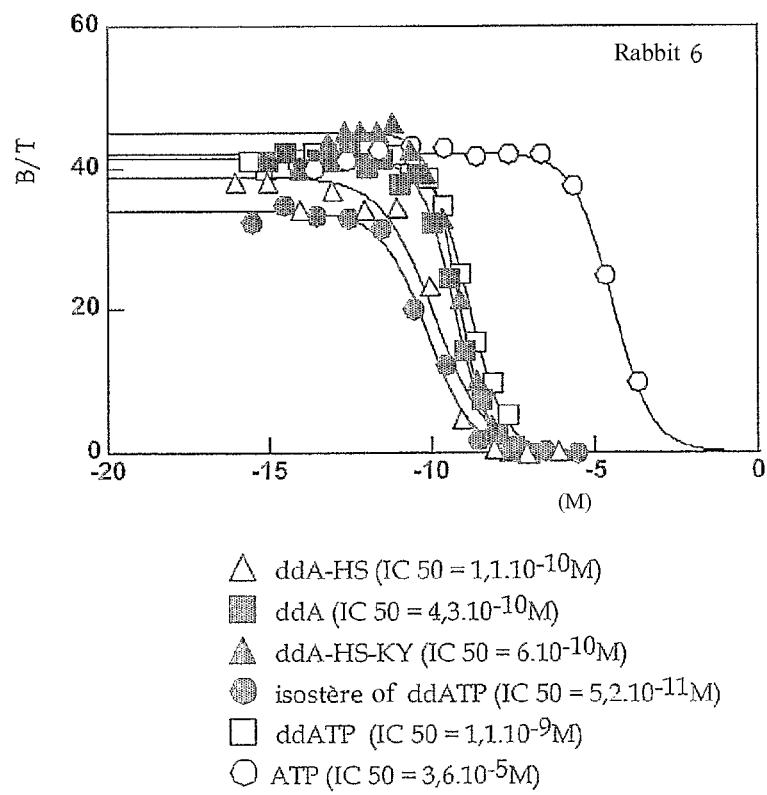
FIG. 9b is a graph showing the analysis of the specificity of the anti-isostere antibody of ddATP. B/T: ratio of bound antigen versus free antigen; (M): log of the final concentration.

We therefore improved the coupling conditions of the ddA to the 2-hydroxy-2,3-allyloxycarbonylbutanoic acid by performing this coupling in the presence of dicyclohexylcarbodiimide (DCC) and 1-hydroxy-7-azabenzotriazole (HOAt) in tetrahydrofuran in order to lead to the formation of 5'-O-((3,4-diallyloxycarboxyl)-3-hydroxy)butanoate-2',3'-didesoxyadenosine (FIG. 8).

The dehydration reaction was eliminated under these conditions.

This coupling was performed in the presence of pyridine for reasons of the solubility of the ddA. The deprotection of the carboxylic acid functional groups was performed in the presence of tetrakis(triphenylphosphine) palladium (0) and diethylamine in methylene chloride.

The 5'-O-(3,4-dicarboxy-3-hydroxy)butanoate-2',3'-didesoxyadenosine was obtained with a quantitative yield after washing the aqueous phase followed by recrystallization.

The same protocol was used for AZT-citrate, d4T-citrate and 3TC-citrate.

II. Preparation of Immunogens. Methods for Coupling or Activation of the Hapten and Coupling to the Carrier Protein.

The coupling to a carrier protein involved activation of one or more carboxylate groups of the hapten. Activation of this carboxylate was implemented either by an alkyl chloroformate (generally ethyl chloroformate) or by an alkyl chlorocarbonate or a carbodiimide in the presence of N-hydroxysuccinimide, which increased the coupling yield to the carrier protein. With regard to the nucleosides possessing a carboxylate group, the activation of this group can be performed with the previously described reagents. In contrast, with an alkyl chloroformate or chlorocarbonate, the activation reaction induced the release of hydrochloric acid in the reaction medium. But in fact the glycosidic bond of the nucleosides was sensitive to the acid medium. It was therefore important to trap this acid by adding to the reaction medium a base such as, e.g., triethylamine. (Kaul, S. et al. 1996. "Specific radioimmunoassay for the measurement of stavudine in human plasma and urine". J. Pharm. Biomed. Anal. 15: 165-174; Ferrua, B. et al. 1994. "Measurement of the anti-HIV agent 2',3'-didehydro-2',3'-dideoxythymidine (D4T) by competitive ELISA". J. Immunol. Methods 176: 103-110, the entire disclosures of which are herein incorporated by reference.)

Five mg of 5'-O-(3,4-dicarboxy-3-didesoxy-3-hydroxy)butanoate-2',3'-adenosine (12 μmoles) were dissolved in 320 μl of anhydrous DMF. This was followed by the addition of 8 mg of dicyclohexylcarbodiimide (3.6 equivalent) and 5 mg of N-hydroxysuccinimide (3.6 equivalent). The reaction mixture was agitated at 4° C. for 3 hours. Then 15 mg of KLH was dissolved in 1 ml of Tris buffer 10 mM at pH 7.7. This was followed by the drop-by-drop addition of the solution containing the activated ester to the KLH solution which had been previously cooled in the refrigerator. The reaction mixture was agitated for 4 hours at 4° C. This solution was stored at −20° C.

The same protocol was used for AZT, d4T and 3TC.

The molar ratio between the carrier molecule and the hapten was an important parameter which enabled production of a conjugate in which the level of incorporation of the hapten was sufficiently elevated so as to induce a maximal immune response leading to the stimulation and activation of the immunocompetent clones. (Cupo A. et al. (1984) "Quantitation and localization of Met-enkephalin-Arg-Gly-Leu in rat brain using highly sensitive antibodies". Neuropeptides 4, 389-401; Cupo A. et al. (1984) "A new immunological approach to the detection and the quantification of the Met5-enkephalin precursors in rat brain". Neuropeptides 4, 375-387; Cupo et al. (1985) "Detection of methionine-enkephalin at the $10^{-16}$ mole level". J. Neuroimmunology, 8: 57-67; Cupo A. et al. (1987) "A new immunization procedure for the obtention of anti-leucine enkephalin antibodies. Part I. Immunization procedure and physicochemical characteristics of antibodies". Neuropeptides 8, 207-219); Cucumel K. et al. (1996) "Production and characteristics of site-directed antibodies against dermorphin and dermorphin-related peptides". Peptides 17, 973-982; Garreau I. et al. (1997) "Radioimmunoassay against the C-part of VV-hemorphin7 peptide: An alternative assay for cathepsin D activity." Peptides 18, 293-300, the entire disclosures of which are herein incorporated by reference.)

III. Preparation of Polyclonal Antibodies

The polyclonal antibodies were produced in the rabbit, according to standard methods.

The immunosera were obtained by immunization of 2 albino rabbits (Combes Breeding Center, Ain, France).

III.1—Immunization Protocol

In the primary immunization, the immunogen was administered to the animal via the intradermal route, but it was also possible to administer it via the subcutaneous, intramuscular or intraperitoneal routes, at the dose of 500 μg of immunogen per immunization and per rabbit diluted by half with Freund's complete adjuvant.

One month after the primary immunization, the immunizations were performed on a booster basis every three weeks over a period of four months. Blood samples were collected ten days after each booster in a heparinized tube so as to avoid coagulation of the blood. After centrifugation, the plasma was collected and stored at −20° C.

III.2 Characterization and Selection of Antibodies Having an Affinity for the ddNTP Derivatives The antibodies having an affinity for the ddNTP derivatives can be identified by immunological techniques either by means of immunoenzymatic determinations or by means of radioimmunological determinations (RIA).

The antibodies obtained above were characterized by radioimmunological determination using as tracer 5'-O-hemisuccinate-2',3'-didesoxyadeonsine coupled to the dipeptide Tyrosyl-Lysine radiotagged with iodine 125.

The comparison of the structures of the isostere of ddATP and the hemisuccinate of ddA showed analogies confirmed by the molecular modeling. This structural analogy was demonstrated experimentally by the fact that the derivative ddA-HS-K-$^{125}$IY is perfectly recognized by the anti-isostere antibody of ddATP as well as the non-radiotagged derivative.

The specificity of these antibodies was studied in relation to different analogues of ddATP. The characteristics of these antibodies were expressed in terms of affinity or sensitivity (or IC50 (M)) and are presented in Table 1 below. The IC50 (M) corresponds to the concentration of non-tagged antigen which inhibits 50% of the antigen-antibody binding.

TABLE 1

| Analogues | IC50 (M) ± SEM |
| --- | --- |
| ddATP | $1.1 \pm 0.1 \times 10^{-9}$ (n = 22) |
| ddA | $4 \pm 0.8 \times 10^{-10}$ (n = 22) |
| ddA-HS-K-Y | $6 \times 10^{-10}$ |
| isostere of ddATP | $5.2 \pm 1.8 \times 10^{-11}$ (n = 3) |
| ATP | $3.6 \times 10^{-5}$ |
| dA | $3 \times 10^{-7}$ |
| adenosine | $2.4 \times 10^{-6}$ |
| adenine | $9 \times 10^{-6}$ |
| ddI | $2 \pm 0.3 \times 10^{-9}$ (n = 10) |
| AMP | nI |
| ADP | nI |
| 3TC | $2 \times 10^{-4}$ |
| ddC | nI |
| AZT | $2 \times 10^{-2}$ |
| d4T | $2 \times 10^{-2}$ | nI: not immunoreactive up to concentrations of $10^{-3}$ M.

Separation by anionic chromatography of the different phosphorylated metabolites stemming from the cellular metabolism of the ddI (ddIMP, ddAMP, ddADP and ddATP) was performed on Sep Pak anionic cartridge by means of a stepwise gradient using different concentrations of KCl (6 ml KCl 50 mM, 10 ml KCl 100 mM and 6 ml KCl 250 mM).

The immunological quantitation of ddATP involved the separation of the ddATP from the other phosphorylated metabolites of the ddA by means of a KCl gradient. It was therefore verified that the concentrations of KCl employed and even higher concentrations (up to 2.5 M) did not inhibit the antigen-antibody interaction.

IV. Preparation of Monoclonal Antibodies

Monoclonal antibodies directed against each nucleoside analogue were prepared by fusion of spleen cells from animals immunized with the corresponding immunogens, followed by immortalization of the stimulated cells secreting antibodies by means of a fusion with murine myeloma lines. This fusion was followed by a selection of the hybrid clones secreting antibodies that present an affinity to said nucleoside analogue.

In order to implement the cellular fusion, use can be made of myeloma lines such as X63ag 8, SP2, NS, Y3, according to the technique described by Kohler G. and Milstein C. (1975) "Continuous cultures of fused cells secreting antibody of predefined specificity". Nature 1975 Aug. 7; 256(5517): 495-7, as well as the protocols described in Cupo A. and Kaldy P. (1987) "Monoclonal anti-idiotypic antibodies which recognized the binding site of delta receptor: fine specificity of the anti-idiotypic antibodies." In "Progress in Opioids Research" J. W. Holaday, P. Y. Law and A. Herz (eds.). NIDA (Rockville, Md., USA) pp. 25-28; Cupo A. et al. (1992) "Monoclonal anti-idiotypic antibodies against 6 opioid receptors as an electron microscopy probe." Eur. J. Cell Biol. 57, 273-284, the entire disclosures of which are herein incorporated by reference.

V. Intracellular Quantification of ddATP. Validation on an In Vitro Cell Model.

The antibodies produced as described above were used for implementing immunological quantifications for the intracellular quantification of the active forms of the nucleosides, notably in human monocytes from the peripheral blood, where the nucleosides were present at very weak concentrations.

A certain number of controls were performed on an in vitro cell model. After separation by density gradient on Ficoll, the blood monocyte cells were incubated with different concentrations of ddI in the RPMI (at the level of $5 \times 10^5$ cells per ml).

The immunoreactivity present in the supernatant was expressed in equivalents (eq.) ddI established in relation to a ddI reference curve, and illustrated in Table 2 below. The ddATP immunoreactivity corresponds to the sum of the immunoreactivities present in the fractions 32-37 stemming from the separation of the intracellular contents on Sep Pak anionic cartridge. The immunoreactivity was expressed in ddATP equivalents in relation to a ddATP reference curve, and is also illustrated in Table 2 below.

TABLE 2

| Concentration of incubated ddI (M) | Concentration of ddI of the supernatant in ddI eq. (M) (m ± SEM) | Intracellular content in ddATP eq. (pmoles/$10^6$) cells (m ± SEM) |
| --- | --- | --- |
| $1 \times 10^{-4}$ | $1.30 \times 10^{-4}$ | 16.2 |
|  | $1.50 \times 10^{-4}$ | 51.0 |
| $1 \times 10^{-5}$ | $3.8 \pm 0.34 \times 10^{-5}$ (n = 2) | $10.4 \pm 0.6$ (n = 2) |
| $5 \times 10^{-6}$ | $5.74 \times 10^{-6}$ (n = 1) | 1.8 (n = 1) |
| $1 \times 10^{-7}$ | $2.74 \times 10^{-7}$ (n = 1) | 0.15 (n = 1) |

Figure 2:
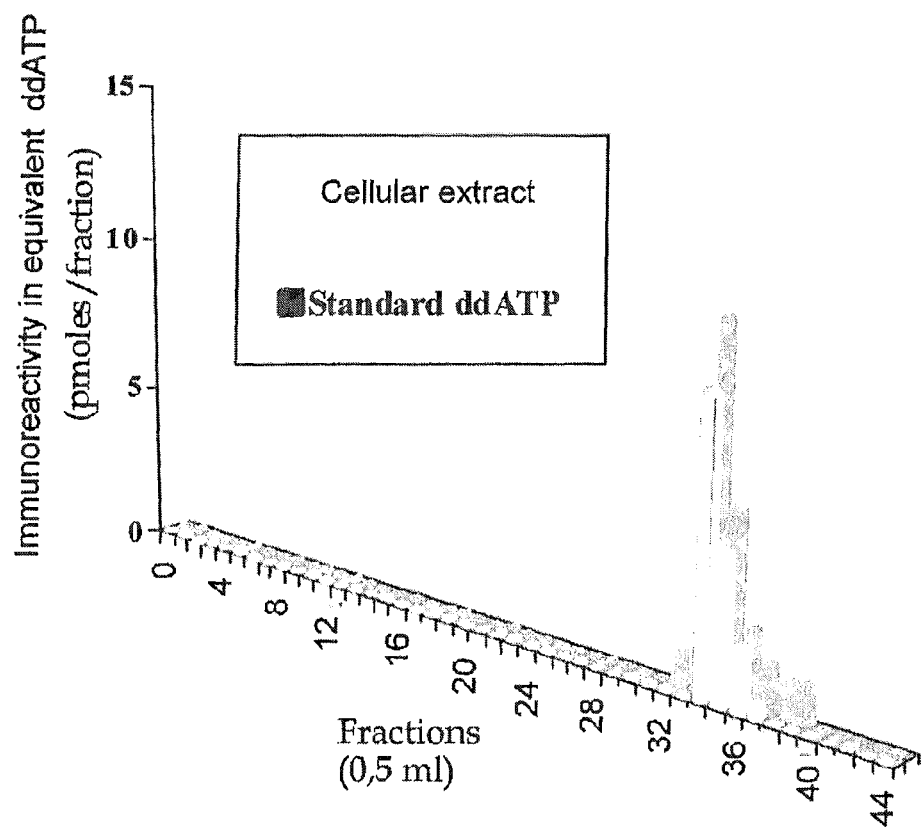
FIG. 2 is a graph showing the determination of the nature of the immunoreactive material present in cells purified by chromatography on anionic cartridge and detected by RIA. At left: Immunoreactivity in ddATP equivalents (pmoles/fraction); In box: Cellular extract/ddATP standard.

The nature of the immunoreactive material present in the culture supernatant and in the intracellular medium was controlled by chromatography on a Sep Pak anionic cartridge. and detected by radioimmunological quantitation. Immunoanalysis of multiple culture supernatants (n=4) showed that 100% of the immunoreactivity is found in fractions 1 to 5, corresponding to the elution volume of the ddI, as illustrated in attached FIG. 1. Analysis of the intercellular contents showed that the immunoreactive contents present in the cells was eluted in the elution volume corresponding to the ddATP with a yield of 92%. This is shown in attached FIG. 2. The absence of immunoreactive material at the retention time of the ddI indicates that the ddI was not detectable in the cells.

Figure 3:
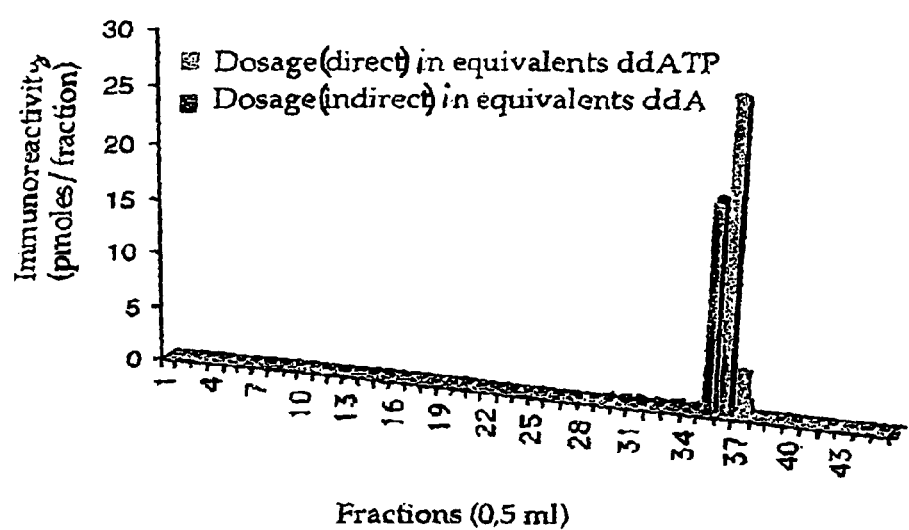
FIG. 3 is a graph showing the characterization of the immunoreactive material present in a cell extract by chromatography on Sep Pak anionic cartridge and radioimmunological detection. At left: Immunoreactivity (pmoles/fraction); Inside graph: Direct quantitation in ddATP equivalents/Indirect quantitation in ddA equivalents.
Figure 4:
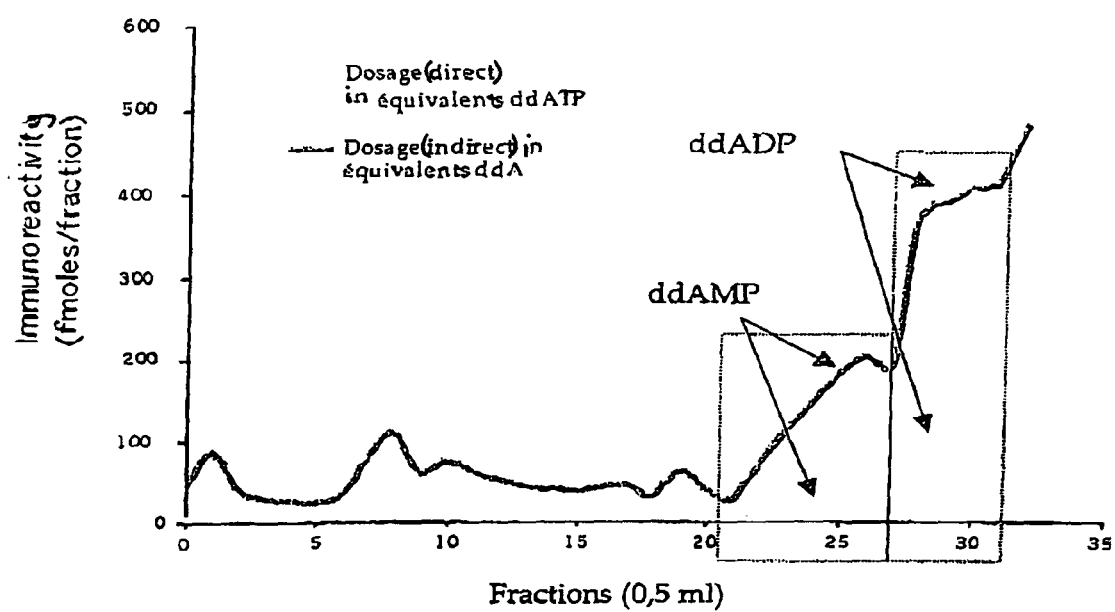
FIG. 4 is a graph showing the immunoreactivity profile of the fractions probably corresponding to ddAMP and ddADP before and after dephosphorylation. At left: Immunoreactivity (fmoles/fraction); Inside graph: Direct quantitation in ddATP equivalents/Indirect quantitation in ddA equivalents.

In order to detect the possible presence of ddAMP and ddADP in the intracellular contents, a quantification after dephosphorylation of the samples was performed after separation on Sep Pak anionic cartridge (indirect quantification expressed in ddA equivalents). This quantification was compared with that performed on the same non-dephosphorylated fractions (direct quantification of ddATP equivalents). The results are presented in attached FIGS. 3 and 4. These results corresponded to the analysis of a cellular extract obtained after incubation of the cells with a ddI concentration of $1.5 \times 10^{-4}$ M.

ddATP was present in fractions 32-37 corresponding to the elution volume of the ddATP standard. The quantity of ddATP detected at the level of these fractions after dephosphorylation represents 93% of the quantity of ddATP before treatment.

When the results are reprocessed by modifying the scale of the immunoreactivities at the level of the fractions preceding the fractions containing ddATP, two projections were seen which could correspond respectively to ddAMP and ddADP. In fact, fractions 24 to 26 and fractions 27 to 30 are fractions in which immunoreactivity is strongly augmented after the treatment with acid phosphatase, indicating that these fractions contained the ddA motif releasable by the enzymatic treatment. The augmentation of the immunoreactivity by a factor of 5 could represent the growth factor which exists between the monophosphorylated and diphosphorylated analogues in relation to ddATP.

VI. Quantification of the Nucleosides in Biological Samples. Clinical Applications.

Blood samples were collected from patients infected with HIV-1 and undergoing treatment comprising administration of ddI. The patients were under the supervision of Professor P. Dellamonica at the Archet Hospital in Nice. The blood samples were collected using cell preparation tubes (CPT) at the rate of two 4-ml tubes for each of the 4 patients participating in this study. Quantification of the ddI in the plasma was performed for each patient and expressed in ddI equivalents. Intracellular quantification of ddATP was performed after chromatography (on Sep Pak anionic cartridge) of the cellular lysates. For each fraction (500 µl), the cellular content of ddATP was determined directly and expressed in ddATP equivalents; quantification was then performed after dephosphorylation and expressed in ddA equivalents.

VI.1 Plasma Determinations of ddATP

The plasma concentrations determined in the four patients were comparable and varied from 2 to $6 \times 10^{-6}$ M. They are illustrated in Table 3 below.

TABLE 3

| Patient | Concentration in ddI eq. ($10^{-6}$ M) | Concentration in ddI eq. (µg/ml) |
|---|---|---|
| BED | 6.10 | 1.44 |
| IPE | 1.95 | 0.46 |
| TRI | 3.20 | 0.76 |
| PRI | 2.95 | 0.70 |

VI.2 Intracellular Determinations of ddATP

The blood components were isolated by centrifugation in cell preparation tubes (CPT, Vacutainer®). The mononuclear cells were washed twice with 15 ml of RPMI medium, centrifuged and counted. The cell counts for each patient are shown in table 4 below. The cell residue was frozen at −70° C.

TABLE 4

| Patient | Number of cells per ml |
|---|---|
| BED | $0.49 \times 10^{-6}$ |
| IPE | $0.98 \times 10^{-6}$ |
| TRI | $1.67 \times 10^{-6}$ |
| PRI | $1.35 \times 10^{-6}$ |

Each cellular sample was processed in the following manner: After lyophilization, the cellular extract was taken up with 1 ml of distilled water. 100 µl was subjected to treatment by acid phosphatase and the ddA content was determined. 200 µl was reserved for direct quantification without purification on the cartridge. The remaining 700 µl was subjected to chromatography on Sep Pak anionic cartridge under the previously described elution conditions. 500-µl fractions were collected. Each fraction was diluted 1.6 times with distilled water then divided into two parts. 400 µl was subjected to direct quantification and 400 µl was dephosphorylated with acid phosphatase in the presence of 1M sodium acetate at 37° C. for 30 minutes. The results of the raw direct and indirect quantitative determinations are presented in summary Table 6.

After purification on anionic cartridge, the immunoreactivity in ddATP equivalents was located principally in fractions 24-31, 32-39 and 42.

The immunoreactivity, as measured by direct quantification, which localized in fraction 42 was not augmented by dephosphorylation. This indicates the presence of ddATP in this fraction. In contrast, the immunoreactivity present at the level of fractions 24-29 and 33-39 was found to be augmented upon indirect quantification (after dephosphorylation), indicating that the epitope recognized by the antibody was unmasked. These fractions, corresponding to the products less retained on the anionic cartridge, should correspond respectively to the monophosphorylated and diphosphorylated products (ddAMP and ddADP) as shown by the results in patient PRI and illustrated in Table 5 below.

TABLE 5

| Fractions | Direct quantification after purification on cartridge (fmoles/$10^6$ cells) | Indirect quantification after purification on cartridge (fmoles/$10^6$ cells) |
|---|---|---|
| 24–29 | 20 | 114 |
| 33–39 | 19 | 252 |
| 42 | 91 | 96 |

VI.3 Summary of the Results

The summary Table 6 below illustrates the results of the intracellular quantitative determinations after purification on anionic cartridge, of the products stemming from the cellular metabolism of the ddI.

TABLE 6

| Patient | Total number of cells $10^6$ (8 ml) | Plasma ddI (M) | ddAMP (fmoles/$10^6$ cells) | ddADP (fmoles/$10^6$ cells) | ddATP (fmoles/$10^6$ cells) |
|---|---|---|---|---|---|
| BED | 3.92 | $6.1 \times 10^{-6}$ | 145 | 535 | 6 |
| IPE | 7.84 | $1.95 \times 10^{-6}$ | 24 | 295 | 15 |
| TRI | 6.7 | $3.20 \times 10^{-6}$ | 62 | 174 | 61 |
| PRI | 10.8 | $2.95 \times 10^{-6}$ | 114 | 252 | 91 |

In this example, ddATP was detected in 4 patients. In one patient, the phosphorylated form of ddA was not detected, whereas in 2 of the 4 patients only the monophosphorylated and diphosphorylated forms were detected. It is probable that in these patients, either the ddATP was not yet synthesized or the kinases involved in the third step of phosphorylation were deficient. The repetition of the quantifications at regular intervals in the patients would allow correlation of the variations in the intercellular concentration of ddATP observed with the indications of the advancement of the HIV infection, the prior treatments and the possible therapeutic success, and would enable implementation of enhanced therapeutic monitoring.

The results of the quantification of the phosphorylated derivatives of ddA obtained by the direct and indirect quantitative determination described above, as well as by quantification after cartridge separation are relatively consistent among each other, with the exception of a single sample.

VI.4 Conclusions

The above examples, with the quantifications performed on four samples, show that the immunological quantification of nucleoside analogues, with the antibodies also prepared according to a method implemented within the framework of the invention, can be used for the quantification of the phosphorylated metabolites of ddA.

The totality of the results presented above show that the immunological test perfected with the antibodies is specific to ddATP. This specificity is ensured by the specificity of the antibodies associated with the purification of the molecules to be quantified when they are in the same compartments (ddI, ddATP, ddADP and ddAMP), and by the fact that they are recognized by the antibodies with different affinities.

A variety of modifications to the embodiments described will be apparent to those skilled in the art from the disclosure provided herein. Thus, our methods may be embodied in other specific forms without departing from the spirit or essential attributes thereof and, accordingly, reference should be made to the appended claims, rather than to the foregoing specification, as indicating the scope of the disclosure.

The invention claimed is:

1. An immunogen comprising a 5'-O-citrate derivative of a nucleoside in which a 5'-O-(3,4-dicarboxy-3-hydroxy)butanoate-2',3'-dideoxy nucleoside is coupled to a carrier molecule through a carboxy group of the 5'-O-derivative, or a nucleoside analog in which an O-(3,4-dicarboxy-3-hydroxy) butanoate ester group formed from the O atom of a —$CH_2$— OH group in the nucleoside analog is coupled to a carrier molecule through a carboxy group of the O-(3,4-dicarboxy-3-hydroxy)butanoate ester group, and which elicits antibodies that bind triphosphorylated nucleosides or triphosphorylated nucleoside analogs.

2. The immunogen of claim 1, wherein the derivative of the nucleoside or of the nucleoside analog is selected from the group consisting of: Acyclovir, adenosine, 2',3'-dideoxyadenosine (ddA), 2',3'-didehydro-2',3'-dideoxythymidine (d4T), 2',3'-dideoxyo-3'-thiacytidine (3TC), 3'-azido-3'-deoxythymidine (AZT), carbovir, cordycepin, cytidine, cytosine-b-D-arabinoside, deoxycytidine, deoxytubercidine, 2'-deoxyuridine, formycin A, formycin B, ganciclovir, guanosine, inosine, puromycin, ribavirin, sangivamycin, thymidine, tubercidin, uridine, abacavir, 3-fluoro-2',3'-dideoxythymidine (FLT), Fura, FdUrd, 6-mercaptopurine 6-MP and AraC.

3. The immunogen of claim 1, wherein the citrate derivative of the nucleoside or of the nucleoside analog is selected from the group consisting of: 6-mercaptopurine (6-MP), cladribine, cytarabine and gemcitabine.

4. The immunogen of claim 1, wherein the carrier molecule is a protein or a polysaccharide.

5. The immunogen of claim 4, wherein the protein is selected from the group consisting of: ovalbumin, bovine serum albumin, limpet hemocyanin, thyroglobin, immunoglobulins, casein, hemoglobin, bacterial toxins, subunit B of cholera toxin, tetanus toxin, diphtheria toxin, lectins, and subunit B of ricin.

6. An immunogen comprising a 5'-O-citrate derivative of a nucleoside in which a 5'-O-(3,4-dicarboxy-3-hydroxy)butanoate-2',3'-dideoxy nucleoside is coupled to a carrier molecule through a carboxy group of the 5'-O-derivative, or a nucleoside analog in which an O-(3,4-dicarboxy-3-hydroxy) butanoate ester group formed from the O atom of a —$CH_2$— OH group in the nucleoside analog is coupled to a carrier molecule through a carboxy group of the O-(3,4-dicarboxy-3-hydroxy)butanoate ester group, and which elicits antibodies that bind triphosphorylated nucleosides or triphosphorylated nucleoside analogs; wherein the derivative of the nucleoside or of the nucleoside analog is selected from the group consisting of: 2',3'-dideoxyadenosine (ddA), 3'-azido-3'-deoxythymidine (AZT), 2',3'-didehydro-2',3'-dideoxythymidine (d4T) and 2',3'-dideoxyo-3'-thiacytidine (3TC).

7. An immunogen comprising a 5'-O-citrate derivative of a nucleoside in which a 5'-O-(3,4-dicarboxy-3-hydroxy)butanoate-2',3'-dideoxy nucleoside is coupled to a carrier molecule through a carboxy group of the 5'-O-derivative, or a nucleoside analog in which an O-(3,4-dicarboxy-3-hydroxy) butanoate ester group formed from the O atom of a —$CH_2$— OH group in the nucleoside analog is coupled to a carrier molecule through a carboxy group of the O-(3,4-dicarboxy-3-hydroxy)butanoate ester group, and which elicits antibodies that bind triphosphorylated nucleosides or triphosphorylated nucleoside analogs; wherein the derivative of the nucleoside or of the nucleoside analog is selected from the group consisting of 2',3'-dideoxyadenosine (ddA), 2',3'-didehydro-2',3'-dideoxythymidine (d4T) and 2',3'-dideoxyo-3'-thiacytidine (3TC).

8. An immunogen comprising a 5'-O-citrate derivative of a nucleoside in which a 5'-O-(3,4-dicarboxy-3-hydroxy)butanoate-2',3'-dideoxy nucleoside is coupled to a carrier molecule through a carboxy group of the 5'-O-derivative, or a nucleoside analog in which an O-(3,4-dicarboxy-3-hydroxy) butanoate ester group formed from the O atom of a —$CH_2$— OH group in the nucleoside analog is coupled to a carrier molecule through a carboxy group of the O-(3,4-dicarboxy-3-hydroxy)butanoate ester group, and which elicits antibodies that bind triphosphorylated nucleosides or triphosphorylated nucleoside analogs; wherein the derivative of the nucleoside or of the nucleoside analog is selected from the group consisting of: acyclovir, adenosine, 2',3'-dideoxyadenosine (ddA), 2',3'-didehydro-2',3'-dideoxythymidine (d4T), 2',3'-dideoxyo-3'-thiacytidine (3TC), carbovir, cladribine, cordycepin, cytarabine, cytidine, cytosine-b-D-arabinoside, deoxycytidine, deoxytubercidine, 2'-deoxyuridine, formycin A, formycin B, ganciclovir, gemcitabine, guanosine, inosine, puromycin, ribavirin, sangivamycin, thymidine, tubercidin, uridine, abacavir, 3-fluoro-2',3'-dideoxythymidine (FLT), Fura, FdUrd, 6-MP and AraC.

* * * * *